(12) United States Patent
Malinin (10) Patent No.: US 9,814,502 B2
(45) Date of Patent: Nov. 14, 2017

(54) BONE PLATE AND METHOD OF USE

(71) Applicant: Theodore I Malinin, Key Biscayne, FL (US)

(72) Inventor: Theodore I Malinin, Key Biscayne, FL (US)

(*) Notice: Subject to any disclaimer, the term of this patent is extended or adjusted under 35 U.S.C. 154(b) by 462 days.

(21) Appl. No.: 14/465,473

(22) Filed: Aug. 21, 2014

(65) Prior Publication Data

US 2016/0051298 A1    Feb. 25, 2016

(51) Int. Cl.
*A61B 17/80*    (2006.01)
*A61B 17/86*    (2006.01)

(52) U.S. Cl.
CPC ......... *A61B 17/8004* (2013.01); *A61B 17/80* (2013.01); *A61B 17/8014* (2013.01); *A61B 17/8052* (2013.01); *A61B 17/8057* (2013.01); *A61B 17/861* (2013.01)

(58) Field of Classification Search
CPC . A61B 17/80; A61B 17/8004; A61B 17/8014; A61B 17/8052; A61B 17/8057
See application file for complete search history.

(56) References Cited

U.S. PATENT DOCUMENTS

| | | | | |
|---|---|---|---|---|
| 7,189,237 | B2* | 3/2007 | Huebner | A61B 17/1728 606/291 |
| 7,537,596 | B2* | 5/2009 | Jensen | A61B 17/1655 606/270 |
| 8,100,953 | B2* | 1/2012 | White | A61B 17/80 606/280 |
| 8,591,554 | B2* | 11/2013 | Raven, III | A61B 17/8061 606/286 |
| 8,652,142 | B2* | 2/2014 | Geissler | A61B 17/15 606/87 |
| 2007/0270859 | A1* | 11/2007 | Companioni | A61B 17/8605 606/279 |
| 2014/0018862 | A1* | 1/2014 | Koay | A61B 17/8057 606/281 |
| 2014/0148859 | A1* | 5/2014 | Taylor | A61B 17/8061 606/282 |

* cited by examiner

*Primary Examiner* — Larry E Waggle, Jr.
(74) *Attorney, Agent, or Firm* — David L. King (57) ABSTRACT

A bone plate assembly has the screws on one plate, either distal or proximal to the fracture, placed through round holes perpendicular to long axis of a first bone thus securing the plate rigidly to the bone on one side relative to the fracture. The screw holes can be either threaded on non-threaded. On the other side of the fracture, the bone fragment is first secured with an inclined screw placed from less than 90 to 10 degrees towards the fracture. As the screw is tightened it advances away from the fracture pulling the first bone, securely attached, plate towards the fracture site and thus compressing the fracture.

8 Claims, 6 Drawing Sheets

BONE PLATE AND METHOD OF USE

FIELD OF THE INVENTION

This invention relates to bone plates for fracture repair and improved methods of repair.

BACKGROUND OF THE INVENTION

Fractures of normal bone usually result from injuries which frequently also involve surrounding tissues. Not all fractures can be treated conservatively as in number of instances treatment by immobilization, traction and other non-surgical methods results in non-unions, delayed unions and malunions. Prolonged immobilization can also lead to stiffness and degeneration of adjacent joints. For these reasons surgical treatment of fractures is often resorted to Anatomical reduction and bone immobilization by internal fixation with plates and screws. This is highly successful, but it too has its limitations not the least of which is stress-shielding. Anatomical reduction and compression of the fracture site with rigid internal fixation are generally achieved by the use of metallic dynamic compression sliding plates and screws. The plates are equipped with elongated holes with angulated sides. This allows bone to move independently of the plates. The holes in the bone plate are configured so as to allow the plate to glide in response to the pressure applied by the screw head and to push the bone fragments to achieve compression of bone fragments against each other. Such fixation usually produces good clinical results. A relatively recent addition to the internal rigid fracture fixation was the advent of locking plates. With conventional plates, screws can move independently from the plate, they may loosen with time. Premature screw loosening produces fracture instability, loss of fracture gap and non-union. Plate to bone compression and friction from the movement of the plate may negatively impact on the blood supply essential to fracture healing and formation of fracture callus, both external and internal. Osteoporotic bone may not be able to withstand high screw torque required to maintain screw-compression plate construct. With locking plates, the screws and plates form a single complex reducing the possibility of hardware failure since the motion between, screws, bone and plate is eliminated. The plate screw assembly distributes stress along the entire length of the plate, thus making it more suited for osteopenic bone and multi segment fractures. Locking screws are not better or worse than conventional screws. They are different. Locking screws use the screw pullout strength more effectively, but cannot compress fractures as conventional screws can. Hybrid plate fixation provides advantages of both techniques. Bridge plating can be performed with conventional, locked or hybrid fixation. The longer the bridge or comminuted segment, the more empty holes in currently available plates. Empty holes can double or triple the plate stresses by concentrating the stress which reduces fatigue life of the plate.

It is well understood that bone healing can also occur as a result of flexible osteosynthesis which provides only relative stability. This method of bone fixation is typically employed in comminuted fractures. The goal of this technique is to maintain length of the bone, its angulation and keep the end portions of fractured bones or joints in correct position without directly lifting or manipulating the fracture zone itself. This can be achieved with locking screws, which as we said do not have the capacity to compress bone fragments.

As is well known to those skilled in the art the bones where fractures occur as well as the types of the fractures vary greatly. Many fractures do not respond well to only rigid internal fixation with compression alone or flexible osteosynthesis with angular stability alone. This precipitated the development of bone plate assemblies which incorporate screws that allow compression or lock into the threaded plate hole. These have been the subject to several patents and publications known to those skilled in the art.

U.S. Pat. No. 8,632,545 B2 discloses the invention relating to a bone plate with a combination hole which can receive a bone screw that can be used to fix bone fragments and also be securely locked in a relationship of angular and axis stability with the bone plate. The invention discloses a bone plate system wherein the bone plate comprises a plurality of holes at least one of which is a combination hole that can receive screw capable of either locking or compressing the plate.

U.S. Pat. No. 6,669,701 discloses a bone plate with at least one hole with a substantially circular outer periphery and a second portion defining an elongated outer periphery, with threads extending over an angle of 100 to 270 degrees at the upper surface of the bone plate and 180 to 230 degrees at the lower surface of the bone plate. The bone plate as disclosed in this patent has only a partial thread in the hole which does not encompass the diameter of the hole completely.

U.S. Pat. No. 8,226,693 reveals an orthopaedic bone bridge for internally fixing and stabilizing fractured bones. It includes first and second bone plates attached to bone by screws. Plates are placed on the opposite sides of the fractures. The plates are mounted on a pair of elongated hollow legs on which the plates are mounted. The second plate is slidably engaged and is movable with respect to the first plate. A cable is attached to the first plate and extends through the legs and around the second plate. The cable provides tensile form between the plates when they are pulled apart thus compressing the fractured bone fragments by forming a bone bridge.

U.S. Pat. No. 5,057,111 reveals non-stress shielding bone healing device which can be with screws, pins or nails for attaching the device to the bone. At least one of two or more openings in the plate is a relaxation opening shaped in part as a truncated spherical section. The plate is preferably a polymer member formed of viscoelastic or resorbable materials.

It is well understood that bone screws used in bone plate assemblies to compress bone fragments also compress the bone plate to underlying bone. This result in stress shielding and undesirable osteopenia or osteoporosis in the bone beneath the plate. The second undesirable effect of compression plates which span the fracture site is the inhibition of the formation of the external callus with consequent weakening of the fracture site.

Bearing these facts in mind the prior art reveals the need for an improved and radically different system of bone plate assemblies.

SUMMARY OF THE INVENTION

The object of the invention is to provide bone plate assemblies secured with screws through threaded or unthreaded holes on a principles different from those employed in a prior art. A bone plate assembly has the screws on one plate, either distal or proximal to the fracture, placed through round holes perpendicular to long axis of a first bone thus securing the plate rigidly to the bone on one side relative to the fracture. The screw holes can be either threaded on non-threaded. On the other side of the fracture, the bone fragment is first secured with an inclined screw placed from less than 90 to 10 degrees towards the fracture. As the screw is tightened it advances away from the fracture pulling the first bone, securely attached, plate towards the fracture site and thus compressing the fracture. The degree of compression is determined by the angle at which it is placed which in turn determines the distance the screw will travel, and pull the already attached plate. Once desired degree of compression is achieved the second plate is further attached with screws placed through the holes at right angles. The holes can be threaded or unthreaded. If the compressing hole is unthreaded a jig or guide directing the placement of the screw at a predetermined angle is another embodiment of the invention. If the hole in the compression plate is with screws, the screws are placed at a predetermined angle. The plate can be marked with the angle θ of the screw and the distance the screw will traverse before the bone fracture placement is complete.

Still another embodiment of the invention is a curvature in the plate which will lay over the actual fracture site thus preventing pressure directly on the fracture site. This is done to prevent inhibition of the external callus formation. The portion of the plate over the fracture site is devoid of holes in order to provide maximum strength to the construct.

BRIEF DESCRIPTION OF THE DRAWINGS

The invention will be described by way of example and with reference to the accompanying drawings in which.

DETAILED DESCRIPTION OF THE INVENTION

With reference to FIGS. 1-7E, the present invention relates to bone plates 3, bone screws 4, 5, 7, and bone plate assemblies used for stabilization and controlled compression of fragments of fractured bone 8. The principles on which this invention is based are different from those described and employed in prior art. In prior art compression is achieved by exerting pressure on the slanted rims of elongated holes in compression plates (dynamic compression plates) and sliding the bone fragment towards another fragment of a fracture bone. The degree of compression is determined empirically, it is not controlled. The present invention employs slanted screws 5 and holes 2 in the plates 3. While one end 3A of the plate 3 is securely attached to a distal or proximal segment 8A of a fracture bone 8 the other side of the plate 3B exerts a pulling force on a fragment 8B secured to the plate 3 through the motion of the screw 5 placed at acute angles θ to the bone fragment 8B. The screw 5 pulls the plate 3 with the attached bone fragment 8A towards the fracture 9 thus compressing it. As the screw 5 placed at an acute angle θ is screwed into the bone 8 it travels away from the fracture 9 pulling the plate 3 with it. The distance the head 5A of the screw 5 will travel will depend on the angle θ the screw 5 is being placed into the bone fragment 8B. Thus the distance (d) the plate 3 will travel and exert compression on the fracture 9 is known in advance. The greater the distance (d) the greater is the degree of compression.

Figure 7A:
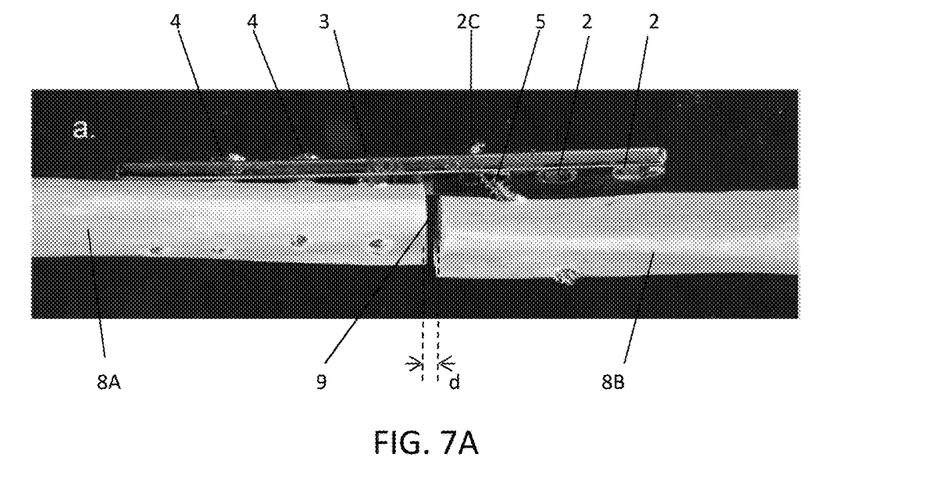
FIGS. 7A-7E are photographs of side and top views of the bone plate of the present invention being installed on a simulated bone.
Figure 7B:
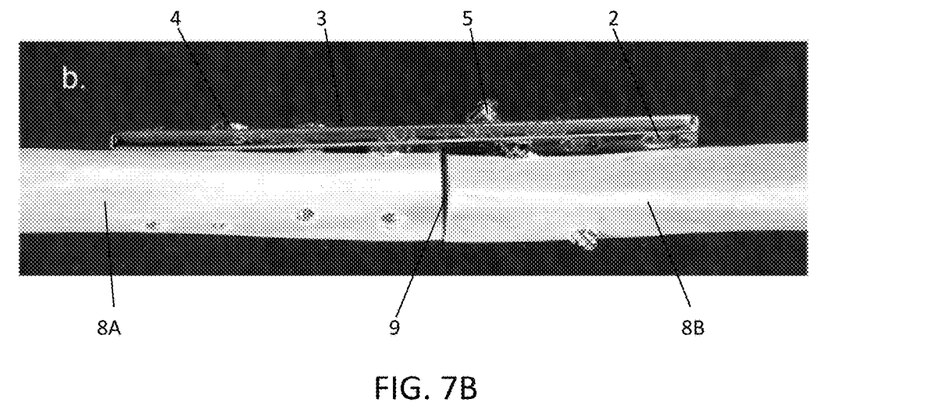
Figure 7C:
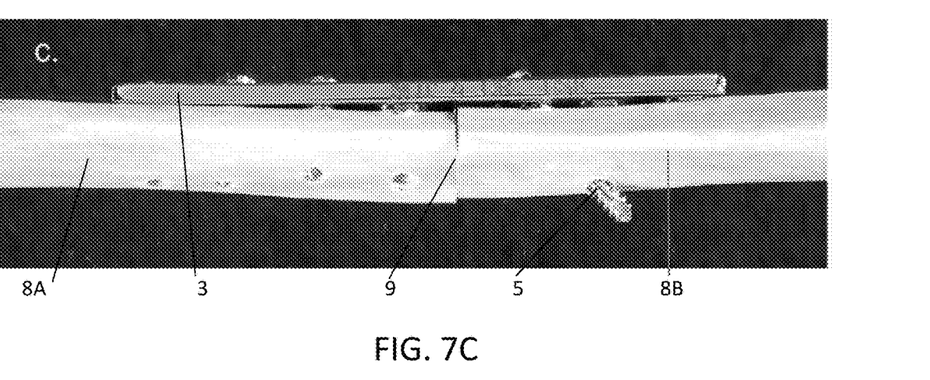
Figure 7D:
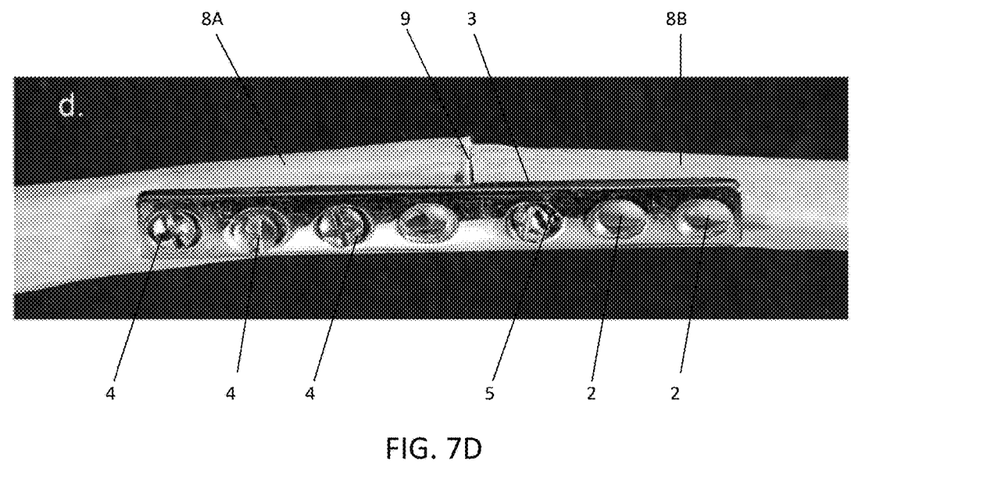
Figure 7E:
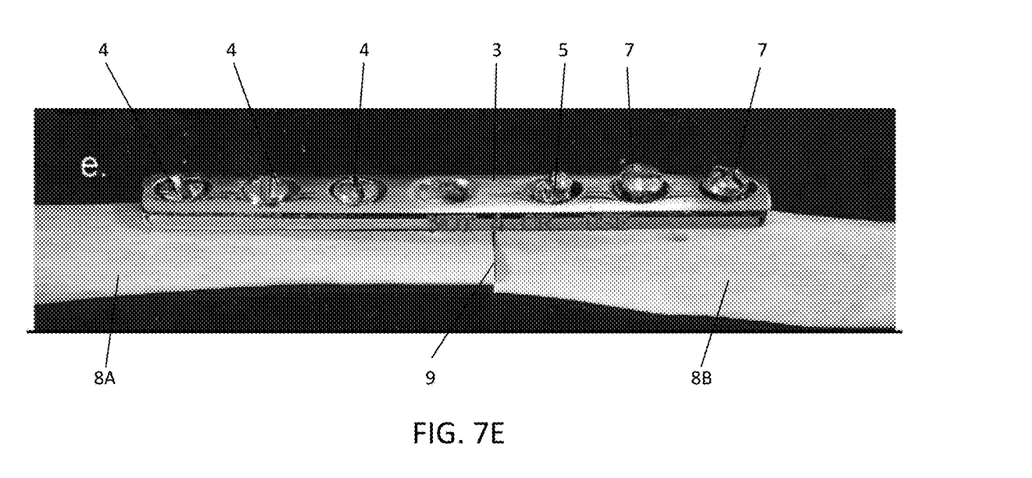

This procedure is best illustrated by the simulation exhibited in FIGS. 7A-7D. In 7A, the cut bone sections 8A and 8B are longitudinally widely spaced as well as vertically offset. The bone 8A is fixed to the plate 3 by the screws 4 perpendicularly fastened to the bone 8A. The inclined screw 5 is shown in the bone fragment or section 8B extending from the compression hole 2C. As the screw 5 tightens, the distance (d) between the bone sections 8A, 8B decreases, see FIG. 7B. On further tightening, the bone sections 8A, 8B are abutting and in compression shown in FIG. 7C. FIG. 7D shows a frontal side view of the bone sections 8A, 8B and the aligned and compressed fracture 9. FIG. 7E is a top perspective view showing the screws 7 completing the fixation of the plate 3 to the bone 8B.

The human skeleton is made up of bones that typically have shafts and heads. It is well understood that fractures of bones are treated differently depending on various factors. Some of these are position of the fracture, number of fragments, condition of bone and damage to the surrounding tissues. Osteopenia and osteoporosis are particularly important consideration. Open treatment of fractures generally employs systems or assemblies of metallic plates with holes to receive the screws. The treatment itself usually includes steps of compressing fractured fragments towards each other. Recent advances in this field include bone plates with holes with threads to accommodate screws with threaded heads, shown in FIG. 3A, which lock the bone plate with the screws thus preventing screw loosening, a relatively frequent occurrence, particularly in osteopenia and osteoporotic bones.

Figure 4:
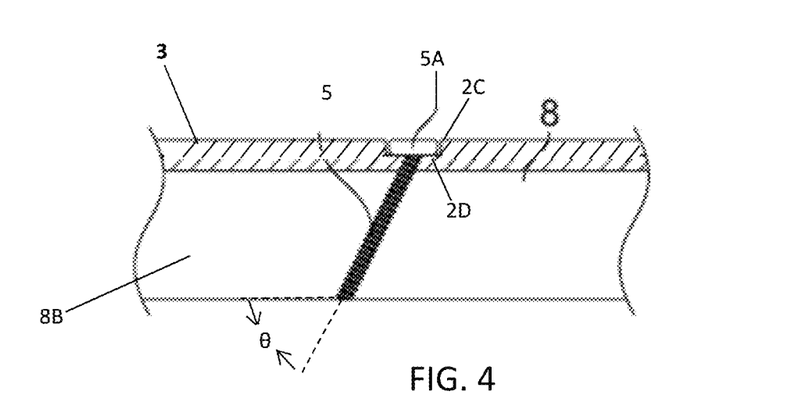
FIG. 4 is a cross sectional view of an exemplary bone screw with an angled head and the bone plate of the present invention.
Figure 9:
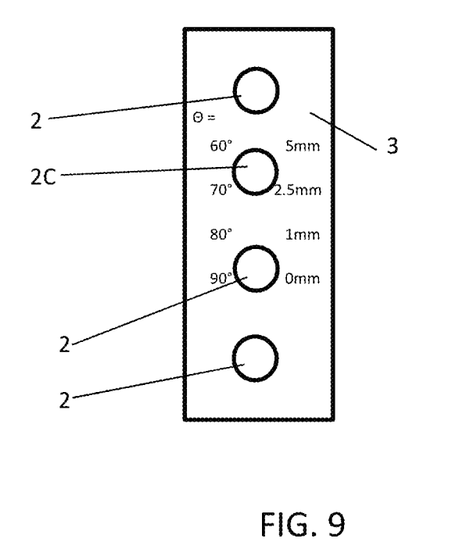
FIG. 9 is a top view of an exemplary plate marked at various angles and corresponding compression distances.

The bone plate 3 of the invention comprises an upper surface 3C and a lower surface 3D. The lower surface 3D is the surface in contact with the underlying bone 8. The plate 3 has a plurality of holes 2 to receive the screws 4, 5, 7. The holes 2, except for the compression holes 2C are designed to accommodate screws 4, 7 for placement perpendicular to underlying bone 8. These holes 2 can be threaded holes 2T to accommodate threaded screw heads or unthreaded holes 2. One or two screw holes 2, 2T are compression holes 2C which are placed at acute angles θ to the long axes of the bones 8. The angles θ are directed away from the fractures 9. As the screws 5 are being screwed in place the head 5A of the screw 5 travels in the direction away from the fracture 9 site. It pulls the plate 3 with it. The distance (d) the screw 5 and head 5A of the screw will travel is determined by the angle θ at which the screw 5 is placed. The hole 2, 2C can be threaded holes 2T to accommodate the placement of the screw 5, as shown in FIG. 4. Proximal portion of the holes 2 can be larger in diameter than the rest of the screw formed as a countersunk hole as illustrated, generally or a counter-bored hole as shown in FIG. 4. The angle θ of the compression screw hole 2C as well as the distance the head 5A of the screw 5 will travel can be marked on the plate 3, shown in FIG. 9. Preferably, this is done in order to allow the surgeon to choose the plate 3 with a predictable compression distance (d). The screw at a 60 degree angle will advance the distal fragment 5 mm, at 70 degree angle it will advance it 2 to 3 mms, at 80 degrees it will advance it 1 mm and at 90 degrees it will, of course, not advance it at all. Another refinement we can add is placing the threads for the locking plates at different angles in the compressing hole.

Figure 8:
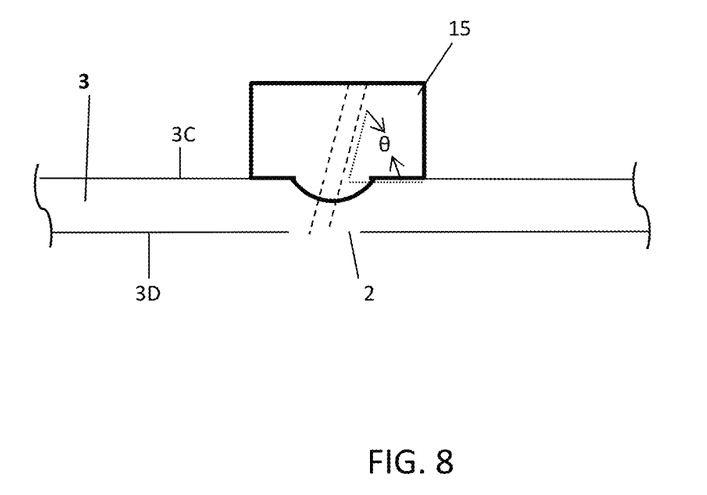
FIG. 8 is a cross sectional view of the drill guide shown with the bone plate of the present invention.

If the plate 3 has a compression hole 2C without threaded screw hole 2T, the angle θ at which the screw 5 is placed can be determined by jigs or guides 15, shown in FIG. 8, designed to pre-drill holes to place screws 5 at various acute angles θ.

Figure 1:
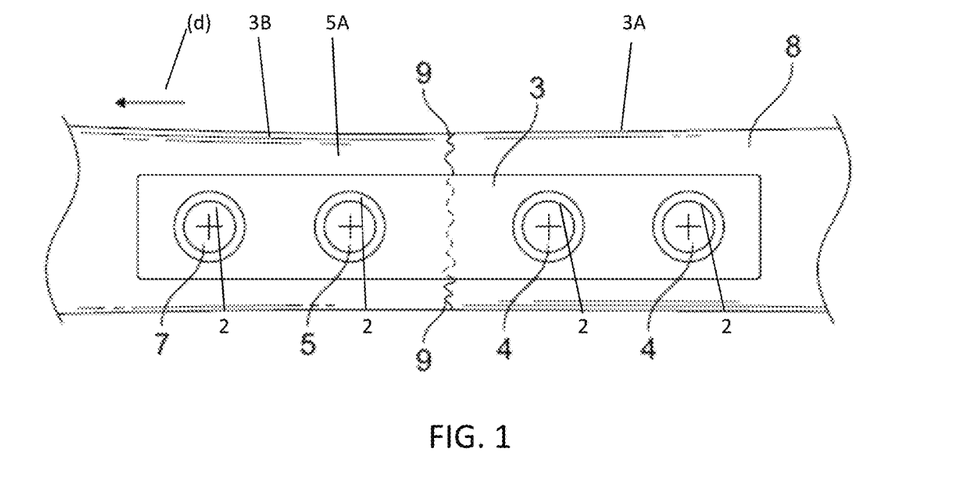
FIG. 1 is a top view of the bone plate made according to the present invention attached to a fractured bone.
Figure 2:
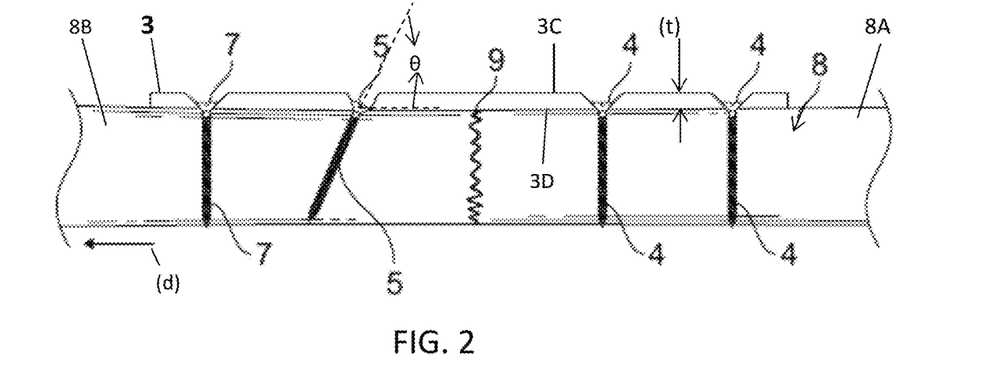
FIG. 2 is a cross sectional view of the fractured bone and bone plate of FIG. 1.
Figure 2A:
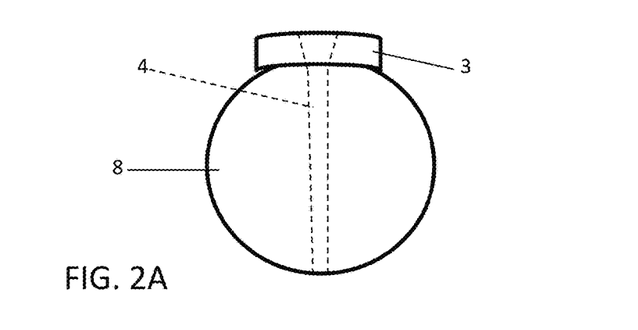
FIG. 2A is an end view of the bone plate of the present invention fixed to a bone.
Figure 3:
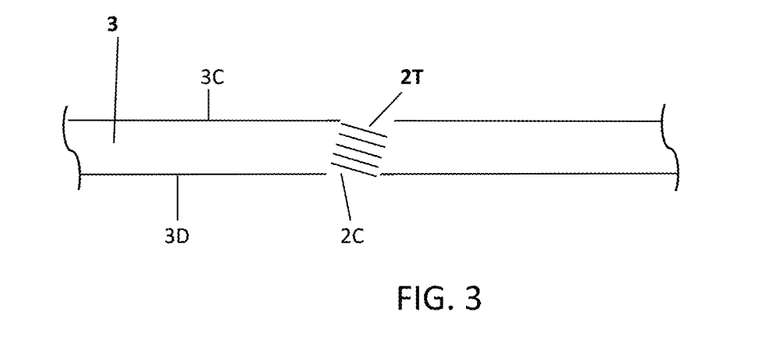
FIG. 3 is a cross sectional view of one embodiment of the bone plate of the present invention showing a hole having angled threads to guide the bone screw.
Figure 3A:
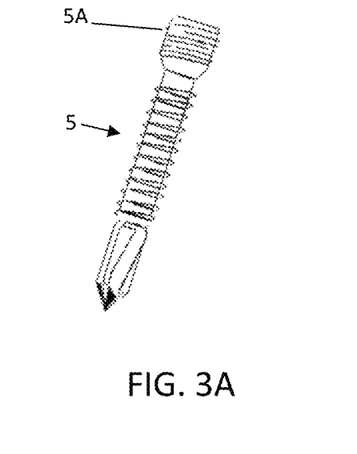
FIGS. 3A and 3B are side views of exemplary bone screws.
Figure 3B:
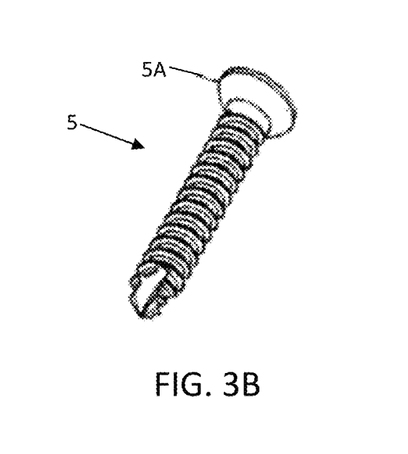

The plates 3 can be made of different thickness (t), preferably from 2 to 5 mm. The plates 3 preferably are concave on the sides to fit the contour of bone 8, as shown in FIG. 2A.

With reference to FIG. 4, the screw 5 as shown has a flat head 5A shown horizontal to the upper surfaces 4C nested in a counterbored hole 2D. The threaded shaft of the screw 5 is inclined by the angle θ. This is one optional assembly.

Figure 5:
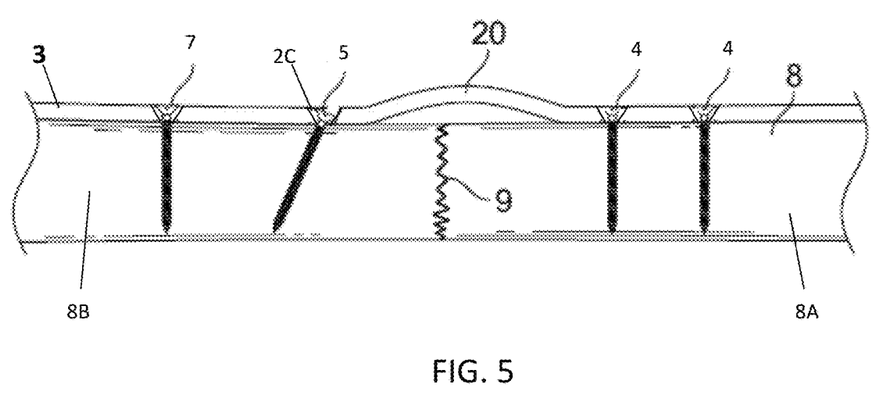
FIG. 5 is a cross sectional view of a second embodiment bone plate of the present invention attached to a fractured bone.

As shown in FIG. 5, in another exemplary embodiment, the bone plates 3 of present invention have upper surface 3C and the lower surface 3D which is concave, said concave lower surface 3D being the bone contacting surface. The plate 3 has a plurality of holes 2 with at least one hole 2 being a compression hole 2C extending at an angle θ from the upper 3C to the lower surface 3D. The mid-portion 20 of the plate is devoid of holes and is a bowed or curved structure with the curve extending above and away from the bone 8. This mid-portion 20 of the plate 3 is placed over the fracture 9 site, and optionally instead of being contoured to the surface of the bone it can be flat. This mid-portion 20 of the plate 3 does not touch the underlying fracture 9 or bone fragments 8A or 8B of the bone 8, thus preventing the inhibition of the external callus encountered with current art compression plates.

Figure 6:
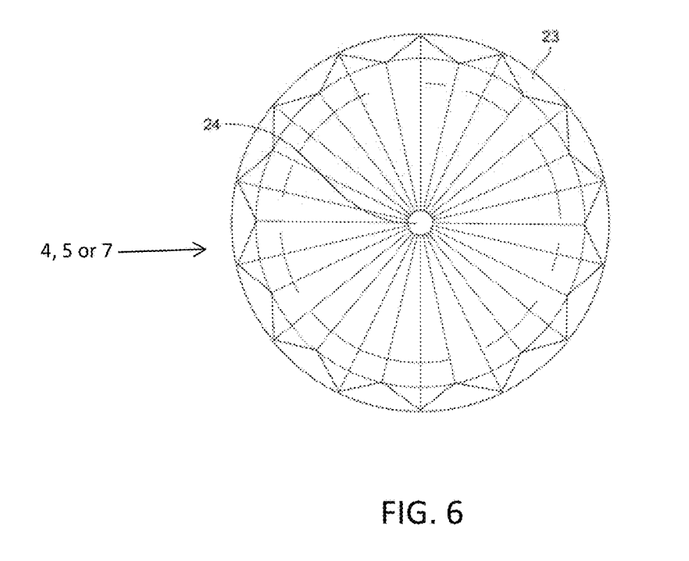
FIG. 6 is a top view of an exemplary screw head for use with the bone plate of the present invention.

With reference to screws, the screws 4, 5, 7 may have any type of mechanical apertures for torqueing and tightening such as common Phillips head, slotted flat or pan heads or Allen heads or as shown in FIG. 6 a faceted head with radially extending petal like slots or channels 23 from a hole 24 to which a complimentary tool (not shown) can be used to drive the screws in place.

The plate 3 with the curved mid-portion 20 can be made sufficiently thick so as to be rigid. Alternative and optionally, the plate 3 can be made thin enough to be flexed slightly toward the bone 8 by the surgeon after the first screws 4 are placed in the plate 3 at that end 3A. By flexing the curved mid-portion 20 inwardly slightly, this lengthens the plate 3 ever so slightly so when the one or more compression screws 5 are placed and the surgeon releases the curved mid-portion 20 the plate 3 shortens slightly to provide a spring loaded additive compressive feature. This effectively allows the plate 3 to mimic dynamic bone fracture plates.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A bone plate assembly for attachment to a bone exhibiting a fracture or break, the bone plate assembly comprising a bone plate, a plurality of bone screws; and
    wherein said bone plate has an upper surface, a bone contacting concave lower surface and a plurality of round holes at least one of which is a compression hole, threaded or unthreaded, placed at an acute angle away from a fracture site;
    said bone screws have at least one compression screw for stabilization and pulling said plate into a compression and stabilization of fractured fragments of bone, wherein said bone plate extends from the bone contacting surface to the upper surface and has round holes placed perpendicular to a long axis of the bone and at least one opening extending at an angle from a round hole on the upper surface to a hole on the bone contacting surface of the plate, the round holes being configured to receive the bone screws including the at least one compression screw and upon tightening the bone screws, the at least one compression screw pulls a bone fragment toward the fracture site while avoiding sliding the plate attached to the bone opposite the fragment site, and wherein said bone plate assembly has a plurality of holes except in a mid-portion of the plate, the mid-portion of the plate being flat and bent away from a bone surface.

2. The bone plate assembly as claimed in claim 1 wherein the at least one compression screw has its head placed at an angle to conform to the upper surface of the plate upon tightening.

3. The bone plate assembly as claimed in claim 1 wherein compression holes are made at different angles to allow for different distances to be traversed by the bone fragment and portion of the plate attached to it.

4. The bone plate assembly as claimed in claim 1 wherein heads of the screws have petal like slots for tightening the screws.

5. The bone plate assembly as claimed in claim 1 wherein tips of the bone screws are self-drilling or self-tapping or a combination of self-drilling and self-tapping.

6. The bone plate assembly as claimed in claim 1 wherein said assembly comprises a drill for placement of drill holes at predetermined acute angles.

7. The bone plate assembly as claimed in claim 1 whereby the plate and or screws are made of stainless steel, cobalt-based alloys, titanium based alloys or biodegradable materials.

8. A method of attaching a bone plate assembly to a bone exhibiting a fracture or break comprising the steps of:
    placing a bone plate over a fracture or break in a bone, the bone plate having an upper surface, a bone contacting concave lower surface and a plurality of round holes at least one of which is a compression hole, threaded or unthreaded, placed at an acute angle away from a fracture site;
    inserting one or more screws into the bone on a first bone section or side relative to the fracture to fix one side of the bone plate to the bone;
    inserting a screw in an angled compression hole of the bone plate on an opposite second bone side or section of the bone relative to the fracture and tightening the angled screw to draw the bone plate and first bone section to the opposite second bone section compressing the fracture, the round holes being configured to receive the bone screws including the screw inserted in the angled compression hole and upon tightening the bone screws, the screw inserted in the angled compression hole pulls a bone fragment toward the fracture site while avoiding sliding the plate attached to the bone opposite the fragment site; and inserting one or more screws in the opposite second bone section to secure the bone plate, wherein all the screw placements are positioned perpendicular to a longitudinal axis of the bone, except the angled screw.

* * * * *